(12) United States Patent
Collier

(10) Patent No.: US 6,202,938 B1
(45) Date of Patent: Mar. 20, 2001

(54) SCENT EMITTING BLIND OPERATING ROD

(76) Inventor: Michael A. Collier, 5959 W. Olive Ave., Glendale, AZ (US) 85311

( * ) Notice: Subject to any disclaimer, the term of this patent is extended or adjusted under 35 U.S.C. 154(b) by 0 days.

(21) Appl. No.: 09/313,325

(22) Filed: May 17, 1999

(51) Int. Cl.⁷ ....................................................... A61L 9/04
(52) U.S. Cl. ............................... 239/34; 239/38; 239/43; 239/44; 239/289
(58) Field of Search ................... 239/34, 37, 38, 239/43, 44, 53, 55, 57, 289

(56) References Cited

U.S. PATENT DOCUMENTS

| | | | | |
|---|---|---|---|---|
| 168,972 | * | 10/1875 | Dayton | 239/57 X |
| 893,740 | * | 7/1908 | Leeper | 239/57 X |
| 1,889,075 | * | 11/1932 | Mills | 239/55 |
| 2,086,046 | * | 7/1937 | Preston | 167/48 |
| 2,418,878 | * | 4/1947 | Harkins | 239/57 X |
| 2,435,096 | * | 1/1948 | Peterson | 239/57 X |
| 2,801,879 | * | 8/1957 | Dick | 239/57 X |
| 3,084,471 | * | 4/1963 | Alspaugh | 43/44 |
| 5,465,521 | * | 11/1995 | Baker et al. | 239/55 X |

FOREIGN PATENT DOCUMENTS

| 142 | * | 1/1914 | (GB) | 239/43 |
|---|---|---|---|---|

* cited by examiner

Primary Examiner—Andres Kashnikow
Assistant Examiner—Robin O. Evans
(74) Attorney, Agent, or Firm—Parsons & Goltry; Robert A. Parsons; Michael W. Goltry

(57) ABSTRACT

Scent emitting blind operating apparatus including a hollow rod, defining an inner chamber, with a closed end and an open end, with the inner chamber of the rod being designed to receive and hold scented material. A blind engaging plug is removably positioned in the open end of the hollow rod for operative engagement with a blind so as to position the inner chamber generally vertically with the closed end directed downwardly. A sleeve of absorbent material is frictionally engaged over the closed end of the hollow rod and an opening is formed through the hollow rod and positioned to communicate the inner chamber with the absorbent material for directing scented material from the inner chamber into the absorbent material.

12 Claims, 1 Drawing Sheet

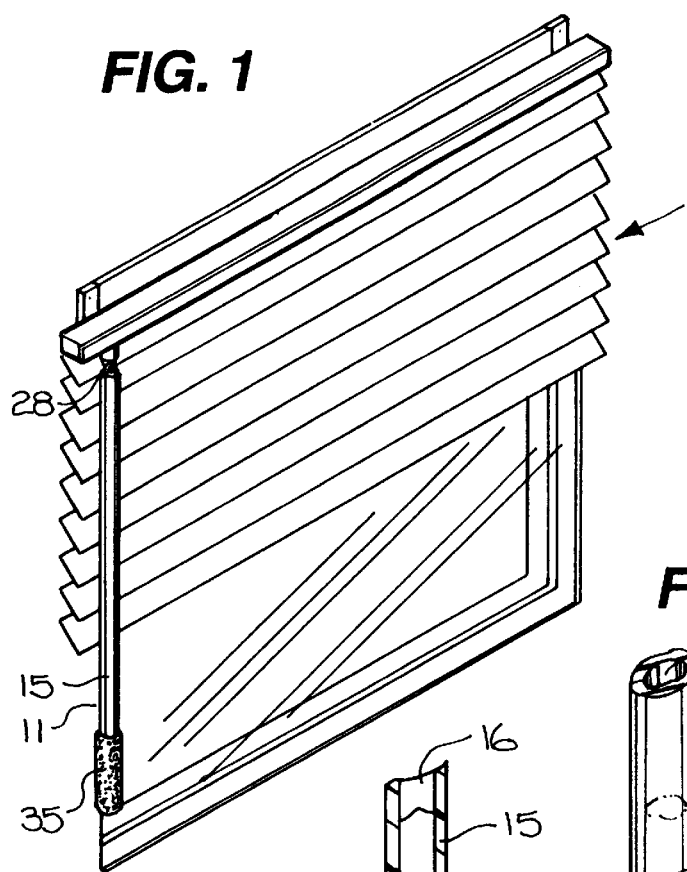
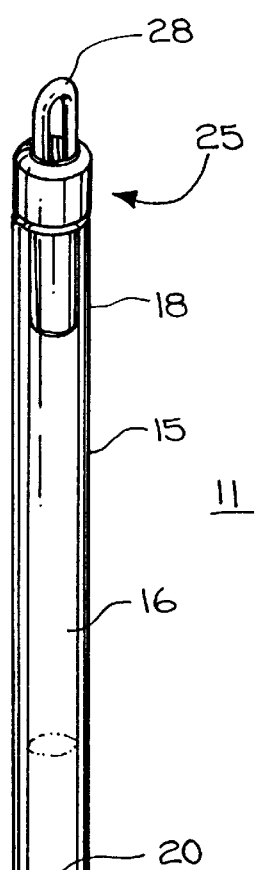
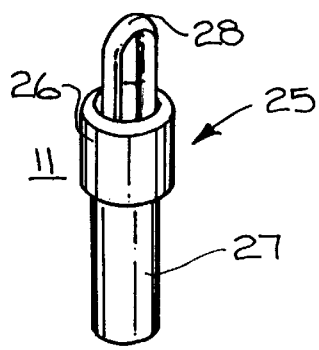
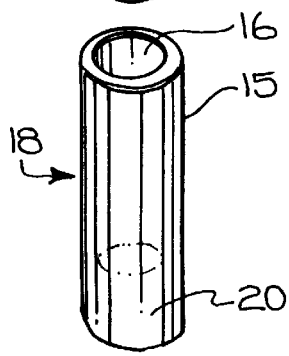
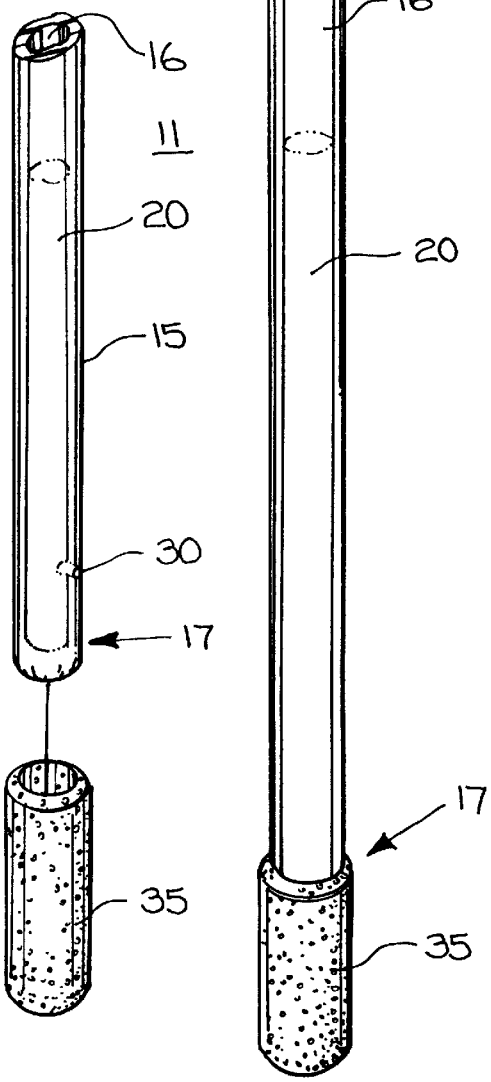

SCENT EMITTING BLIND OPERATING ROD

FIELD OF THE INVENTION

This invention relates to apparatus for dispersing scented material in a room.

More particularly, the present invention relates to convenient, reusable apparatus for dispersing scented material in a room.

BACKGROUND OF THE INVENTION

At the present time it is common to provide various means throughout areas inhabited by humans (e.g. living areas, office space, etc.) for dispersing scents that are either simply pleasing and/or may be to cover less desirable scents. In a traditional manner, small dishes or containers of scented material (e.g. pot pourri) are strategically positioned around an area to provide desirable fragrance. Some throw-away plastic containers filled with scented material can be purchased, which containers are simply set in strategic places where malodorous smells are apt to occur. Recently, several products are being marketed which actively produce scents, one of which is a device containing an electrical coil and a scented material. The device is plugged into an electrical outlet to activate the electrical coil and cause the scented material to be essentially "boiled off" into the surrounding air.

The problem with all scent dispersing devices presently being used is that they require containers that must be set about and require additional area, generally on top of some other piece of furniture. Generally, the cheap throw-away containers are not aesthetically pleasing and must be positioned where they are not immediately obvious. Some of these devices are rechargeable and some must be periodically replaced with new devices once the scented material has been completely used. Also, in most instances it is difficult to determine when the scented material in these devices is low or completely used.

It would be highly advantageous, therefore, to remedy the foregoing and other deficiencies inherent in the prior art.

Accordingly, it is an object of the present invention to provide new and improved scent emitting blind operating apparatus.

Another object of the invention is to provide new and improved scent emitting blind operating apparatus which is not immediately obvious and does not detract from the aesthetics of a room.

And another object of the invention is to provide new and improved scent emitting blind operating apparatus which is convenient to use.

Still another object of the present invention is to provide new and improved scent emitting blind operating apparatus which provides a convenient way to determine the extent of the scented material therein and which can be easily recharged with scented material when required.

Yet another object of the invention is to provide new and improved scent emitting blind operating apparatus which does not require any additional area but which can be conveniently positioned without being obvious.

SUMMARY OF THE INVENTION

Briefly, to achieve the desired objects of the instant invention in accordance with a preferred embodiment thereof, provided is scent emitting blind operating apparatus including a body defining an inner chamber with a closed end and an open end with the inner chamber being designed to receive and hold scented material. A blind engaging plug is removably positioned in the open end of the inner chamber for operative engagement with a blind so as to position the inner chamber generally vertically with the closed end directed downwardly. An opening is provided through the body in communication with the inner chamber and an outer surface for gradually dispensing scented material from the inner chamber to a surrounding atmosphere.

The desired objects of the instant invention are further achieved in accordance with a preferred method of dispersing scent in a room including the steps of providing scent emitting blind operating apparatus including a body defining an inner chamber with a closed end and an open end, the inner chamber being designed to receive and hold scented material, a blind engaging plug removably positioned in the open end for operative engagement with a blind so as to position the inner chamber generally vertically with the closed end directed downwardly, and an opening through the body communicating the inner chamber with an outer surface for gradually dispensing scented material from the inner chamber to a surrounding atmosphere. The plug is removed from the open end and scented material is introduced into the inner chamber. The plug is then replaced in the open end and operatively engaged with a blind in the room so that the body is positioned with the closed end directed generally downwardly to allow the scented material to gradually escape through the opening into the room.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which:

FIG. 1 is an isometric view of a typical window blind incorporating scent emitting blind operating apparatus in accordance with the present invention;

FIG. 2 is an enlarged isometric view of the scent emitting blind operating apparatus of FIG. 1;

FIG. 3 is an isometric view, partially exploded and portions thereof broken away, of the scent emitting blind operating apparatus of FIG. 2;

FIG. 4 is a sectional view, portions thereof broken away, of the spent emitting blind operating apparatus of FIG. 2; and FIG. 5 is an isometric view, partially exploded and portions thereof broken away, of the scent emitting blind operating apparatus of FIG. 2.

DETAILED DESCRIPTION OF THE PREFERRED EMBODIMENT

Turning now to the drawings in which like reference characters indicate corresponding elements throughout the several views, attention is first directed to FIG. 1 which illustrates a typical window blind 10 incorporating scent emitting blind operating apparatus 11 in accordance with the present invention. While a blind formed of a plurality of horizontal slats (sometimes referred to as a Venetian blind) is utilized herein for purposes of explanation, it should be understood by those skilled in the art that the term "blind" as used herein is intended to include any of the various curtains, shades, etc. currently operable with elongated rods or other hanging devices). Blind operating devices which incorporate elongated plastic rods and are utilized to control standard blinds, curtains, shades, etc. are well known in the art and the operation thereof will not be elaborated upon.

Generally, apparatus 11 includes a body defining an inner chamber with a closed end and an open end. The inner chamber is designed to receive and hold scented material. A blind engaging plug is removably positioned in the open end of the inner chamber for operative engagement with a blind so as to position the inner chamber generally vertically with the closed end directed downwardly. An opening is formed through the body to provide communication between the inner chamber and an outer surface for gradually dispensing the scented material from the inner chamber to a surrounding atmosphere. Here it should be understood that apparatus 11 may be constructed with a variety of shapes depending generally upon the type of blind with which it is being used.

Turning more specifically to FIG. 2, an enlarged view is illustrated of a preferred embodiment of scent emitting blind operating apparatus 11. In this preferred embodiment, the body of apparatus 11 includes an elongated hollow rod 15 defining an inner chamber 16 having a closed end 17 and an open end 18. Inner chamber 16 is designed to receive and hold scented material 20, generally in a fluid form. In this preferred embodiment, hollow rod 15 is formed of a plastic tubular material which is sufficiently transparent (i.e. clear, translucent, etc.) to allow an operator to look at it and determine at least approximately the amount of scented material 20 remaining in hollow rod 15. It will be understood by those skilled in the art that hollow rod 15 can be formed of any material such as wood, plastic, metal, etc., and can be opaque, transparent or translucent, etc.

Referring additionally to FIG. 3, a blind engaging plug 25 is removably positioned in open end 18 of inner chamber 16 to prevent the flow of scented material 20 outwardly through open end 18 once it has been placed in inner chamber 16. Also, plug 25 fits sufficiently tight to allow blind 10 to be manipulated with apparatus 11. Plug 25 has a cap 26 with an outer diameter approximately the same as the outer diameter of hollow rod 15 and a downwardly extending portion 27 with an outer diameter approximately the same as the inner diameter of hollow rod 15 so that plug 25 can be frictionally engaged in open end 18 of hollow rod 15. Here it should be understood that many different forms of plug 25 can be utilized (e.g. a slightly tapered downwardly extending portion 27, threaded outer diameter of portion 27 and the inner surface of hollow rod 15, etc.) to ensure a snug fit even after many cycles of use. Also, plug 25 is constructed for operative engagement with a blind (e.g. blind 10) so as to position inner chamber 16 generally vertically with closed end 17 directed downwardly. In this embodiment a U-shaped metal clip 28 is fixedly engaged in cap 26 and is formed so as to engage an operative portion of blind 10 in a well known manner. Thus, apparatus 11, is connected to blind 10 for normal opening, closing, raising, and lowering operations and is easily removable so as to be recharged with scented material 20 when required.

Referring now to FIG. 4, at least one small opening 30 is formed through hollow rod 15 to provide communication between inner chamber 16 and an outer surface for gradually dispensing scented material 20 from inner chamber 16 to a surrounding atmosphere. Here it should be understood that opening 30 must be small enough to allow only a very small amount of scented material 20 to issue or emanate to the outer surface of hollow rod 15 so that scented material 20 is gradually dispensed. In one embodiment, one or more capillary holes or capillary tubes can be formed in the wall of hollow rod 15 through which a liquid scented material 20 will issue only as fast as it can be evaporated.

Referring additionally to FIG. 5, an absorbent material is affixed to an outer surface of hollow rod 15 in communication with opening 30 and adjacent closed end 17. In this preferred embodiment, the absorbent material is provided in the form of a sleeve 35 of absorbent material which is constructed to be frictionally engaged over closed end 17 of hollow rod 15. The absorbent material can be any of the well known spongy materials presently available commercially which will receive scented material 20 from opening 30 and quickly distribute it throughout the absorbent material for maximum dispersing effect. While scented material 20 could be simply dispersed by means of one or more openings 30, it will be understood by those skilled in the art that sleeve 35 greatly enhances the distribution of scented material 20 since it greatly enlarges the area from which evaporation can occur. Also, the absorbent material is provided in the form of sleeve 35 so that it can be easily removed from hollow rod 15 and cleaned when necessary or replaced.

Thus, the present invention includes a method of dispersing scent in a room including the step of providing scent emitting blind operating apparatus having a body defining an inner chamber with a closed end and an open end, the inner chamber being designed to receive and hold scented material, a blind engaging plug removably positioned in the open end for operative engagement with a blind so as to position the inner chamber generally vertically with the closed end directed downwardly, and an opening through the body communicating the inner chamber with an outer surface for gradually dispensing scented material from the inner chamber to a surrounding atmosphere. The method further includes the steps of removing the plug from the open end of the inner chamber, introducing scented material into the inner chamber, replacing the plug in the open end, and operatively engaging the plug with a blind in the room so that the body is positioned with the closed end directed generally downwardly to allow the scented material to gradually escape through the opening into the room.

Thus, new and improved scent emitting blind operating apparatus has been disclosed in which the amount of scented material can be readily ascertained and recharged if required. Further, if absorbent material is used to more readily disperse the scented material, it can be provided in the form of a sleeve which can be easily removed and cleaned or replaced. The new and improved scent emitting blind operating apparatus does not require any additional space or area and is not immediately obvious, so that it does not detract from the aesthetics of a room.

Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. Scent emitting blind operating apparatus comprising:
   a body, including an elongated hollow rod, defining an inner chamber with a closed end and an open end, the inner chamber being designed to receive and hold scented material;
   a blind engaging plug removably positioned in the open end for operative engagement with a blind so as to position the inner chamber generally vertically with the closed end directed downwardly, the blind engaging plug includes an elongated piece of material formed to frictionally fit into the open end of the hollow rod and further includes a metal connector designed to be engaged with a control member of a blind; and an opening through the body communicating the inner chamber with an outer surface for gradually dispensing scented material from the inner chamber to a surrounding atmosphere.

2. Scent emitting blind operating apparatus as claimed in claim 1 wherein the elongated hollow rod is formed of a transparent material.

3. Scent emitting blind operating apparatus as claimed in claim 1 wherein the opening through the body is substantially a capillary tube.

4. Scent emitting blind operating apparatus comprising:

a body defining an inner chamber with a closed end and an open end, the inner chamber being designed to receive and hold scented material;

a blind engaging plug removably positioned in the open end for operative engagement with a blind so as to position the inner chamber generally vertically with the closed end directed downwardly;

an opening through the body communicating the inner chamber with an outer surface for gradually dispensing scented material from the inner chamber to a surrounding atmosphere; and an absorbent material affixed to an outer surface of the body in communication with the opening and adjacent the closed end.

5. A method of dispersing scent in a room comprising the steps of:

providing scent emitting blind operating apparatus including a hollow rod shaped body defining an inner chamber with a closed end and an open end, the inner chamber being designed to receive and hold scented material, a blind engaging plug removably positioned in the open end for operative engagement with a blind so as to position the inner chamber generally vertically with the closed end directed downwardly, and an opening through the body communicating the inner chamber with an outer surface for gradually dispensing scented material from the inner chamber to a surrounding atmosphere;

removing the plug from the open end and introducing scented material into the inner chamber;

replacing the plug in the open end and operatively engaging the plug with a blind in the room so that the body is positioned with the closed end directed generally downwardly to allow the scented material to gradually escape through the opening into the room; and frictionally engaging a sleeve of absorbent material over the closed end of the hollow rod shaped body.

6. A method of dispersing scent in a room as claimed in claim 5 including in addition a step of removing, cleaning, and replacing the sleeve of absorbent material over the closed end of the hollow rod shaped body.

7. A method of dispersing scent in a room as claimed in claim 5 wherein the step of providing the hollow rod shaped body includes providing a transparent hollow rod shaped body and the method further includes the step of viewing the scented material within the transparent hollow rod shaped body through the transparent hollow rod shaped body to determine when sufficient scented material has been introduced into the transparent hollow rod shaped body.

8. A scent emitting blind operating rod comprising:

a hollow rod, defining an inner chamber, with a closed end and an open end, the inner chamber being designed to receive and hold scented material;

a blind engaging plug removably positioned in the open end of the hollow rod for operative engagement with a blind so as to position the inner chamber generally vertically with the closed end directed downwardly;

a sleeve of absorbent material frictionally engaged over the closed end of the hollow rod; and an opening through the hollow rod positioned to communicate the inner chamber with the absorbent material for directing scented material from the inner chamber into the absorbent material.

9. A scent emitting blind operating rod as claimed in claim 8 wherein the blind engaging plug includes an elongated piece of material formed to frictionally fit into the open end of the hollow rod and further includes a metal connector designed to be engaged with a control member of a blind.

10. A scent emitting blind operating rod as claimed in claim 8 wherein the elongated hollow rod is formed of a transparent material.

11. A scent emitting blind operating rod as claimed in claim 8 wherein the opening through the body is substantially a capillary tube.

12. Scent emitting blind operating apparatus comprising:

a body, including an elongated hollow rod, defining an inner chamber with a closed end and an open end, the inner chamber being designed to receive and hold scented material;

a blind engaging plug removably positioned in the open end for operative engagement with a blind so as to position the inner chamber generally vertically with the closed end directed downwardly;

an opening through the body communicating the inner chamber with an outer surface for gradually dispensing scented material from the inner chamber to a surrounding atmosphere; and a sleeve of an absorbent material frictionally engaged over the closed end of the elongated hollow rod.

* * * * *